(12) United States Patent
Nejati

(10) Patent No.: US 11,185,280 B2
(45) Date of Patent: Nov. 30, 2021

(54) SYSTEM AND METHOD FOR FACILITATING ANALYSIS OF A WOUND IN A TARGET SUBJECT

(71) Applicant: KroniKare Pte Ltd, Singapore (SG)

(72) Inventor: Hossein Nejati, Singapore (SG)

(73) Assignee: KroniKare Pte Ltd, Singapore (SG)

( * ) Notice: Subject to any disclaimer, the term of this patent is extended or adjusted under 35 U.S.C. 154(b) by 0 days.

(21) Appl. No.: 16/754,337

(22) PCT Filed: Oct. 17, 2017

(86) PCT No.: PCT/SG2017/050519
§ 371 (c)(1),
(2) Date: Apr. 7, 2020

(87) PCT Pub. No.: WO2018/217162
PCT Pub. Date: Nov. 29, 2018

(65) Prior Publication Data
US 2020/0330028 A1    Oct. 22, 2020

(51) Int. Cl.
*A61B 5/00*      (2006.01)
*G06T 7/62*      (2017.01)
(Continued)

(52) U.S. Cl.
CPC ............ *A61B 5/445* (2013.01); *A61B 5/0036* (2018.08); *A61B 5/015* (2013.01); *A61B 5/447* (2013.01); *A61B 5/7264* (2013.01); *G01J 5/0025* (2013.01); *G06K 9/46* (2013.01); *G06K 9/628* (2013.01); *G06N 3/08* (2013.01);
(Continued)

(58) Field of Classification Search
CPC ..... A61B 5/0002; A61B 5/0064; A61B 5/015; A61B 5/0531; A61B 5/1075; A61B 5/446; A61B 5/447; A61B 5/7264; A61B 5/441–445; G06K 2209/05; G06K 9/00208; G06K 9/46; G06K 9/4628; G06K 9/628; G06T 2207/30088; G06T 17/00; G06T 2207/10024; G06T 2207/20081; G06T 2207/20084; G06T 2207/30004;
(Continued)

(56) References Cited

U.S. PATENT DOCUMENTS

| 2010/0185064 A1* | 7/2010 | Bandic | .................. A61B 5/415 600/306 |
| 2013/0116573 A1* | 5/2013 | Herman | ............... A61B 5/0064 600/474 |

(Continued)

OTHER PUBLICATIONS

International Search Report and Written Opinion dated Dec. 22, 2017 in International Patent Application No. PCT/SG2017/050519, filed Oct. 17, 2017, 10 pages.

(Continued)

*Primary Examiner* — Amelie R Davis
(74) *Attorney, Agent, or Firm* — Kilpatrick Townsend & Stockton LLP

(57) ABSTRACT

A system and method for facilitating analysis of a wound in a target subject is provided. The method comprises obtaining one or more digital images of at least a portion of the wound; extracting a plurality of feature vectors from the one or more digital images; and identifying, using a first trained deep neural network, a type of wound tissue based on the plurality of extracted feature vectors.

18 Claims, 7 Drawing Sheets

(51) Int. Cl.
| | |
|---|---|
| G06T 7/11 | (2017.01) |
| A61B 5/01 | (2006.01) |
| G01J 5/00 | (2006.01) |
| G06K 9/46 | (2006.01) |
| G06K 9/62 | (2006.01) |
| G06N 3/08 | (2006.01) |
| G06T 7/00 | (2017.01) |
| G06T 17/00 | (2006.01) |

(52) U.S. Cl.
CPC .............. *G06T 7/0012* (2013.01); *G06T 7/11* (2017.01); *G06T 7/62* (2017.01); *G06T 17/00* (2013.01); *A61B 5/6898* (2013.01); *G01J 2005/0077* (2013.01); *G06T 2207/20084* (2013.01); *G06T 2207/30004* (2013.01)

(58) Field of Classification Search
CPC .......... G06T 7/0012; G06T 7/11; G06T 7/62; G06N 3/0454; G06N 3/08
See application file for complete search history.

(56) References Cited

U.S. PATENT DOCUMENTS

| | | | |
|---|---|---|---|
| 2015/0119721 A1 | 4/2015 | Pedersen et al. | |
| 2015/0150457 A1* | 6/2015 | Wu ...................... | A61B 5/6898 600/425 |
| 2016/0100790 A1* | 4/2016 | Cantu .................. | A61B 5/0064 600/306 |
| 2016/0284084 A1 | 9/2016 | Gurcan et al. | |
| 2017/0076446 A1 | 3/2017 | Pedersen et al. | |
| 2017/0231550 A1* | 8/2017 | Do ...................... | G06K 9/4652 382/128 |
| 2018/0279943 A1* | 10/2018 | Budman ............... | G06T 7/0014 |

OTHER PUBLICATIONS

International Preliminary Report on Patentability dated Dec. 9, 2018 in International Patent Application No. PCT/SG2017/050519, filed Oct. 17, 2017, 18 pages.

Veredas, F.J., et al. "Wound image evaluation with machine learning", Neurocomputing, vol. 164, Issue C., Sep. 21, 2015, DOI: https://doi.org/10.1016/j.neucom.2014.12.091, p. 112-122.

Mukherjee, R., et al. "Automated Tissue Classification Framework for Reproducible Chronic Wound Assessment", Biomed Research International, vol. 2014, Article ID 851582, published Jul. 8, 2014, DOI: https://doi.org/10.1155/2014/851582, 10 pages.

Wannous, H., et al., "Combined Machine Learning with Multi-view Modeling for Robust Wound Tissue Assessment", Conference: VISAPP 2010—Proceedings of the Fifth International Conference on Computer Vision Theory and Applications, Angers, France, vol. 1, May 17-21, 2010, p. 92-104.

Wang, C., et al., "A unified framework for automatic wound segmentation and analysis with deep convolutional neural networks", 37$^{th}$ Annual International Conference of the IEEE Engineering in Medicine and Biology Society, vol. 2015, Aug. 29, 2015, DOI: 10.1109/EMBC.2015.7318881, p. 2415-2418.

Wu, K., et al., "Mobile Wound Assessment using Novel Computer Vision Methods", Journal of the American College of Surgeons, vol. 219, Issue 3, Aug. 22, 2014, DOI:https://doi.org/10.1016/j.jamcollsurg.2014.07.150, p. S64-S65.

Barone, S., et al. "Assessment of Chronic Wounds by Three-Dimensional Optical Imaging Based on Integrating Geometrical, Chromatic, and Thermal Data", Proceedings of the Institution of Mechanical Engineers, Part H: Journal of Engineering in Medicine, vol. 225, No. 2, Published Jul. 2, 2010, DOI:https://doi.org/10.1243/09544119JEIM705, p. 181-193.

Khong, P.C.B., et al., "Modeling the Construct of an Expert Evidence-Adaptive Knowledge Base for a Pressure Injury Clinical Decision Support System", Informatics, vol. 4, Issue 20, published Jul. 12, 2017, DOI:https://doi.org/10.3390/informatics4030020, p. 1-16.

* cited by examiner

SYSTEM AND METHOD FOR FACILITATING ANALYSIS OF A WOUND IN A TARGET SUBJECT

TECHNICAL FIELD

The present disclosure relates to systems and methods for facilitating analysis of a wound in a target subject.

BACKGROUND

Wound assessment and analysis is critical to determine the extent of an injury and also to evaluate the progress of wound healing. Traditional wound assessment requires obtaining tissue from the wound and sending the tissue of the wound to a laboratory for analysis. Such an assessment of the wound is time-consuming as it requires several hours to several days in order to determine the extent of the injury and the necessary treatment to be administered to the wound.

In recent times, analysis of wounds can be performed by different imaging devices, such as a hand-held camera, a thermal imaging device or an infrared camera. However, there are many drawbacks. For example, existing thermal imaging devices are bulky and a lot of time is wasted to setup the device before taking the image of the wound. Further, analysis of the captured image takes a long time and the devices are also unable to provide a complete analysis of the wound, and therefore leave the nurse with several other manual assessments, and thus not providing a cost-effective add-on to the nurse abilities.

In addition, nurses need to detect seven different types of tissue to determine wound condition and the required treatment. On the other hand, current approaches can only detect/analyse up to three types of wound tissues, i.e. necrotic, slough and granulation. By only detecting three types of wounds, current automatic tissue assessment systems combine all three types of granulation into one class labelled as granulation, and also combine slough and infected types into one class, labelled as slough. This can mislead medical practitioners, leading to misdiagnosis, mistreatment, and further complications. Current thermal imaging devices and infrared camera are also expensive and other types of devices, such as metal oxide gas sensors use contact sensors which will need the device to be in contact with the wound.

A need therefore exists to provide a method and system for facilitating analysis of a wound in a target subject that seeks to address at least some of the above problems.

SUMMARY

According to a first aspect of the present invention, there is provided a method for facilitating analysis of a wound of a target subject, the method including: obtaining one or more digital images of at least a portion of the wound; extracting a plurality of feature vectors from the one or more digital images; and identifying, using a first trained deep neural network, a type of wound tissue based on the plurality of extracted feature vectors.

In an embodiment, the method may include processing the one or more digital images of the wound for segmentation of the wound from other surrounding tissue of the wound prior to extracting the plurality of feature vectors from the one or more digital images.

In an embodiment, the step of processing the one or more digital images of the wound for segmentation of the wound may include: down-sampling the one or more digital images of the wound; coarse segmentation of the down-sampled one or more digital images; and refinement of the coarse segmented one or more digital images.

In an embodiment, two digital images of the wound may be obtained separately from two digital image capturing devices spaced apart from each other, and the method may further include: constructing a three-dimensional model of the wound based on the two digital images of the wound; and processing the three-dimensional model of the wound for segmentation of the wound from other surrounding tissue of the wound prior to extracting the plurality of feature vectors from the one or more digital images.

In an embodiment, the method may include determining at least one critical dimension of the wound based on the segmented three-dimensional model.

In an embodiment, a second trained deep neural network may be used to facilitate construction of the three-dimensional model of the wound.

In an embodiment, two digital images of the wound may be obtained and one of the two digital images may include a thermal image of the wound, and the method may further include: extracting thermal signature data from the thermal image; and identifying a secondary complication based on the extracted thermal signature data.

In an embodiment, the secondary complication may include at least one of: blood-circulation, wound infection, skin-related condition, undermining of wound and pressure point.

In an embodiment, the identified type of wound tissue may include at least one of: necrotic, slough, healthy granulation, unhealthy granulation, hyper granulation, infected and epithelization.

In an embodiment, the method may include: receiving wound data corresponding to one or more of: (i) the identified type of wound tissue, (ii) the dimension of the wound, and (iii) the identified secondary complication; generating a coded vector based on the wound data using a deep hashing function, the coded vector representing a consolidated assessment of the wound; retrieving, from a database, treatment data corresponding to the coded vector.

According to a second aspect of the present invention, there is provided a system for facilitating analysis of a wound of a target subject, the system including: one or more image capturing modules configured to obtain one or more digital images of at least a portion of the wound; a processor module configured to extract a plurality of feature vectors from the one or more digital images; and a first neural network module configured to implement a first trained deep neural network for identifying a type of wound tissue based on the plurality of extracted feature vectors.

In an embodiment, the processor module may be further configured to process the one or more digital images of the wound for segmentation of the wound from other surrounding tissue of the wound prior to extracting the plurality of feature vectors from the one or more digital images.

In an embodiment, the processor module may be further configured to: perform down-sampling the one or more digital images of the wound; perform coarse segmentation of the down-sampled one or more digital images; and perform refinement of the coarse segmented one or more digital images, for segmentation of the wound from other surrounding tissue of the wound.

In an embodiment, the system may include two digital image capturing devices spaced apart from each other and configured to separate obtain two digital images of the wound, wherein the processor module is further configured to: construct a three-dimensional model of the wound based on the two digital images of the wound; and process the three-dimensional model of the wound for segmentation of the wound from other surrounding tissue of the wound prior to extracting the plurality of feature vectors from the one or more digital images.

In an embodiment, the processor module may be further configured to determine at least one critical dimension of the wound based on the segmented three-dimensional model.

In an embodiment, the system may include a second neural network module configured to implement a second trained deep neural network to facilitate construction of the three-dimensional model of the wound.

In an embodiment, two digital images of the wound may be obtained and one of the two digital images comprises a thermal image of the wound, wherein the processor module may be further configured to: extract thermal signature data from the thermal image; and identify a secondary complication based on the extracted thermal signature data.

In an embodiment, the processor module may be further configured to: receive wound data corresponding to one or more of: (i) the identified type of wound tissue, (ii) the dimension of the wound, and (iii) the identified secondary complication; generate a coded vector based on the wound data using a deep hashing function, the coded vector representing a consolidated assessment of the wound; retrieve, from a database, treatment data corresponding to the coded vector.

BRIEF DESCRIPTION OF THE DRAWINGS

Embodiments will be better understood and readily apparent to one of ordinary skill in the art from the following written description, by way of example only, and in conjunction with the drawings, in which.

DETAILED DESCRIPTION

Figure 1:
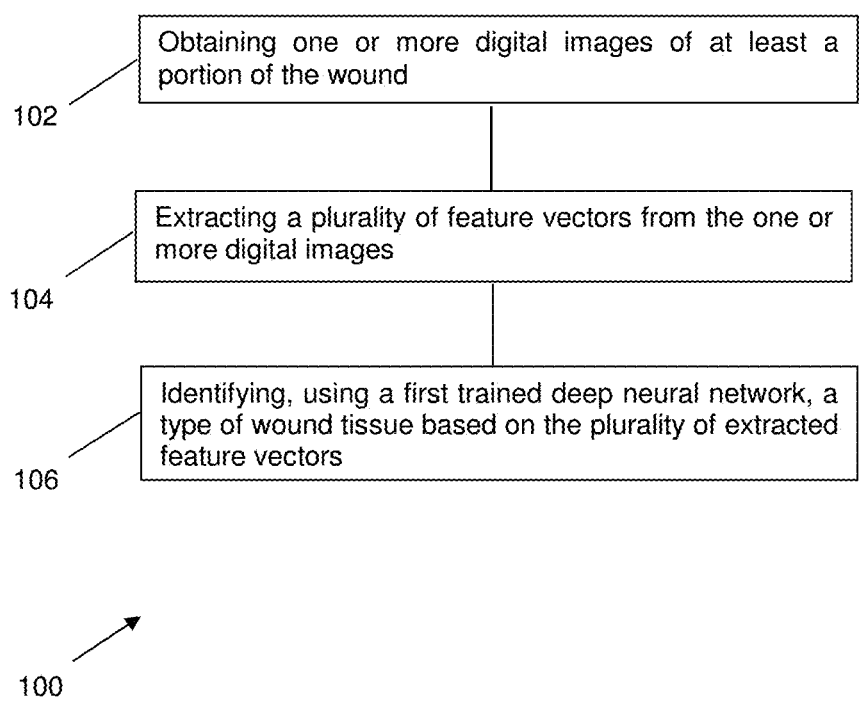
FIG. 1 shows a flow chart illustrating a method for facilitating analysis of a wound of a target subject, according to an example embodiment.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", "identifying", "authorizing", "verifying" or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a computer or other device selectively activated or reconfigured by a computer program stored in the computer. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the disclosure.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM mobile telephone system. The computer program when loaded and executed on such a computer effectively results in an apparatus that implements the steps of the preferred method.

FIG. 1 shows a flow chart 100 illustrating a method for facilitating analysis of a wound of a target subject according to an example embodiment. At step 102, one or more digital images are obtained of at least a portion of the wound or a part of body suspected to develop a wound in near future (e.g. back side of a bed-bound patient). At step 104, a plurality of feature vectors are extracted from the one or more digital images. At step 106, a type of wound tissue is identified using a first trained deep neural network based on the plurality of extracted feature vectors.

The method may further comprise processing the one or more digital images of the wound for segmentation of the wound from other surrounding tissue of the wound prior to extracting the plurality of feature vectors from the one or more digital images. The step of processing the one or more digital images of the wound for segmentation of the wound may comprise: down-sampling the one or more digital images of the wound; coarse segmentation of the down-sampled one or more digital images; and refinement of the coarse segmented one or more digital images. Two digital images of the wound may be obtained separately from two digital image capturing devices spaced apart from each other. The method may further comprise: constructing a three-dimensional model of the wound based on the two digital images of the wound; and processing the three-dimensional model of the wound for segmentation of the wound from other surrounding tissue of the wound prior to extracting the plurality of feature vectors from the one or more digital images.

The method may also further comprise determining at least one critical dimension of the wound based on the segmented three-dimensional model. A second trained deep neural network may be used to facilitate construction of the three-dimensional model of the wound. Two digital images of the wound may be obtained and one of the two digital images may comprise a thermal image of the wound. The method may also include extracting thermal signature data from the thermal image and identifying a secondary complication based on the extracted thermal signature data. The secondary complication may include at least one of: blood-circulation, wound infection, skin-related condition, undermining of wound and pressure point and the identified type of wound tissue may include at least one of: necrotic, slough, healthy granulation, unhealthy granulation, hyper granulation, infected and epithelization. The method may also include receiving wound data corresponding to one or more of: (i) the identified type of wound tissue, (ii) the dimension of the wound, and (iii) the identified secondary complication; generating a coded vector based on the wound data using a deep hashing function, where the coded vector represents a consolidated assessment of the wound; and retrieving treatment data corresponding to the coded vector from a database.

Figure 2:
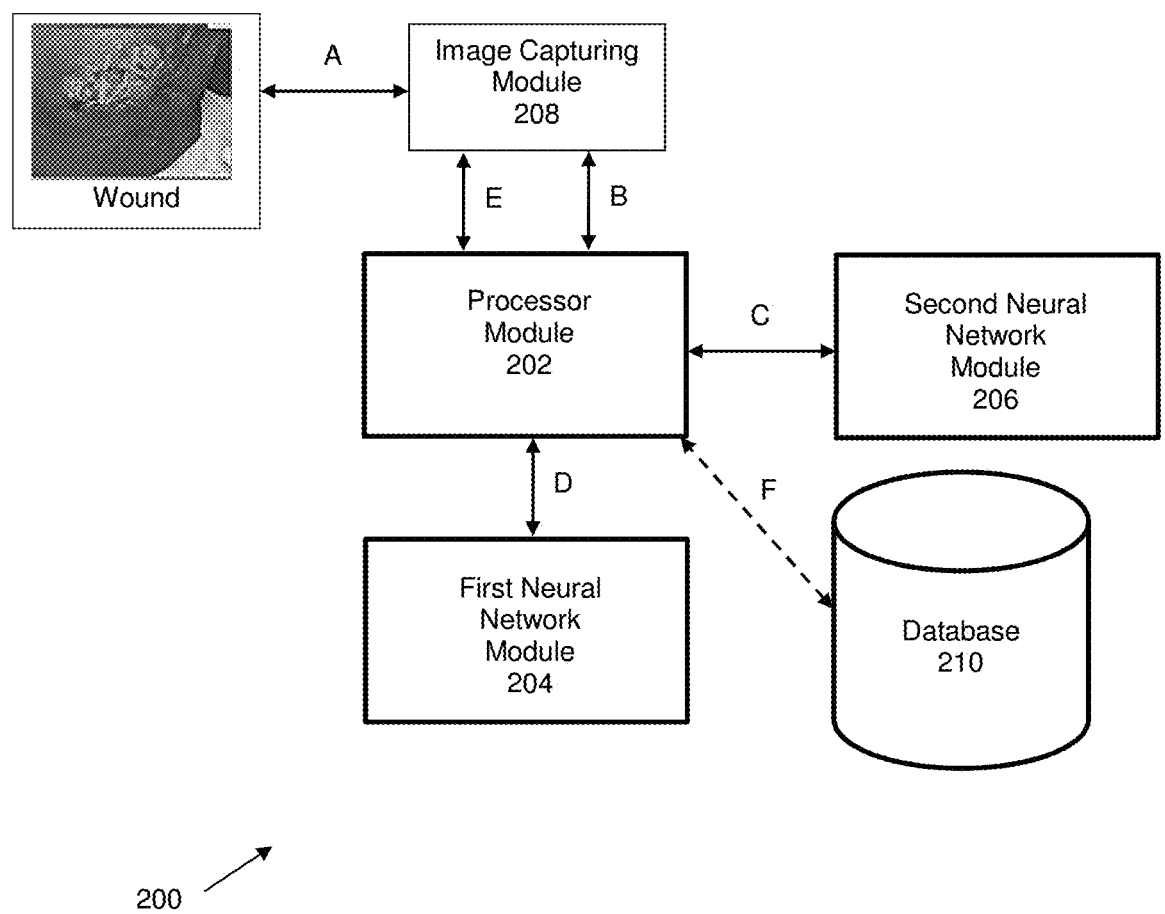
FIG. 2 shows a schematic diagram illustrating the flow of information in a system for facilitating analysis of a wound of a target subject, according to an example embodiment.

FIG. 2 shows a schematic diagram illustrating the flow of information in a system 200 for facilitating analysis of a wound of a target subject. The system 200 comprises a processor module 202, a first neural network module 204, a second neural network module 206, a database 210 and an image capturing module 208. The image capturing module 208 is configured to obtain one or more digital images of at least a portion of the wound. The processor module 202 is configured to extract a plurality of feature vectors from the one or more digital images. The first neural network module 204 is configured to implement a first trained deep neural network for identifying a type of wound tissue based on the plurality of extracted feature vectors. The image capturing module 208 is in communication with the processor module 202, which in turn is in communication with the first neural network module 204, the second neural network module 206 and the database 210.

Figure 3:
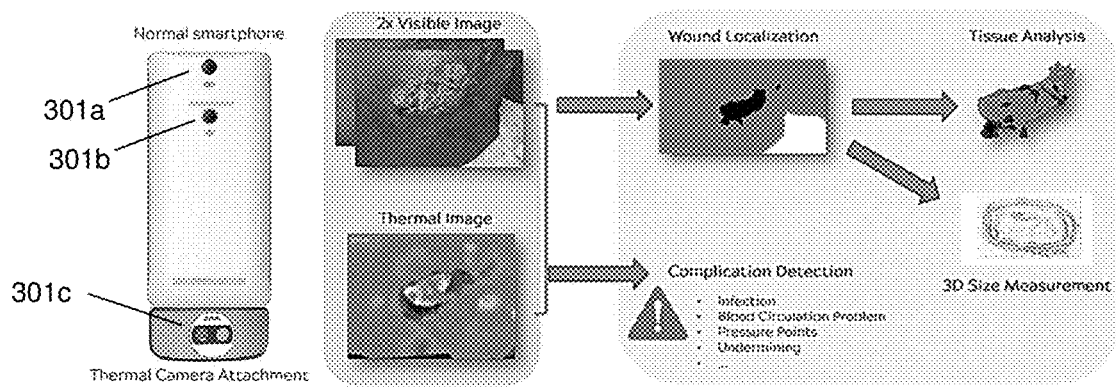
FIG. 3 shows a side view of a smartphone with two digital image capturing devices, according to an example embodiment.

At step A in FIG. 2, the image capturing module 208 captures digital images of the wound. The digital images may include one or more visible-light images and/or one or more infrared images and the image capturing module 208 may be integrated with a smartphone as shown in FIG. 3. The image capturing module 208 may comprise two or more digital image capturing devices spaced apart from each other and configured to separately obtain two digital images of the wound, such as infrared, thermal and/or visible-light images (see FIG. 3). For example, the image capturing module 208 may comprise two visible-light image capturing devices 301a, 301b and a thermal image capturing device 301c as shown in FIG. 3. The digital images are subsequently sent to the processor module 202 at step B in FIG. 2 for segmentation of the wound from other surrounding tissue of the wound in the digital images.

Image segmentation is performed using visual features of isolated object or objects separated by boundaries to partition an image into several segments. Image segmentation is needed to locate the region-of-interest for analysis and assessment of the wound. In particular, the wound needs to be initially localized in the received digital images, for example visible-light images, before other analysis of the wound can be performed. Accordingly, image segmentation has to be performed under simultaneous memory and computation constraints of portable devices, such as smartphones.

In an implementation, image segmentation involves pixel-domain down-sampling of the digital images and includes two main steps: Firstly, coarse segmentation is performed on the down-sampled digital images and secondly, refinement is then applied to the coarse segmentation results of the digital images. In addition, a framework is provided which may enable competitive accuracy for image segmentation. The framework may include examining the effect of down-sampling on segmentation using a signal processing analysis. Such an analysis may determine the uncertain regions on the wound, for example, small image regions where pixel labels are uncertain after the coarse segmentation. Further, an efficient Minimum Spanning Tree (MST)-based algorithm is applied to propagate the labels into the uncertain regions. Such a framework and method of image segmentation not only may improve segmentation accuracy, but may use less computation time and memory than existing methods, thereby making it suitable for image analysis applications on portable devices.

Further, the processor module 202 may also construct a three-dimensional model of the wound based on the two digital images of the wound and process the three-dimensional model of the wound for segmentation of the wound from other surrounding tissue of the wound prior to extracting the plurality of feature vectors from the one or more digital images.

A full three-dimensional model of the wound can be reconstructed because of the presence of stereo vision. This may be possible by having the two digital image capturing devices (e.g. two visible-light cameras 301a, 301b as shown in FIG. 3) with known distance from each other to capture images of the wound, and the three-dimensional model can be reconstructed using camera intrinsic properties and triangulation approach.

In an embodiment, a compressed second neural network module 206 may be configured to implement a second trained deep neural network to facilitate construction of the three-dimensional model of the wound in order to construct a three-dimensional model estimation of the wound on a portable device (see Step C of FIG. 2). For example, the second neural network module 206 may be running on the portable device together with the processor module 202. The second trained deep neural network may be compressed into the architecture of the smartphone such that the processor module 202, together with the second neural network module 206, and may be able to rapidly estimate the dimensions of the wound on the phone with lower energy consumption.

Figure 4A:
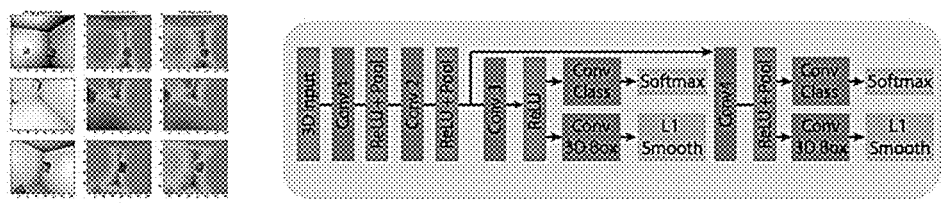
FIGS. 4a and 4b shows a flow chart illustrating a method of training a second deep neural network, according to an example embodiment.
Figure 4B:
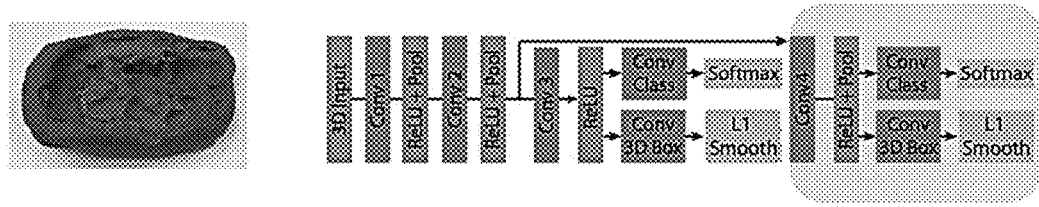

FIG. 4a shows a flowchart illustrating a method of training a second trained deep neural network. The second deep neural network may be trained using a large number of synthetic three-dimensional image pairs to obtain desirable accuracy on the three-dimensional estimation, as shown in FIG. 4a. Subsequently, the second deep neural network may be fine-tuned based on real images from wound clay models (as shown in FIG. 4b). Such a two-step training of the second deep neural network may increase efficiency as synthetic images with known dimensions can be obtained with ease. Subsequently, when the second deep neural network is trained on general three-dimensional estimation, problem-specific training images may be implemented to fine-tune for wound measurement.

Alternatively, the second trained deep neural network may be located in a server (not shown in FIG. 2). As more computational power and energy is available on the server, a higher definition three-dimensional model may be achieved from the two digital images obtained from the two digital image capturing devices. The three-dimensional model of the wound may be reconstructed from a video of the wound captured by the portable device (e.g. a smartphone) using structure from motion (SfM). Specifically, a fast and accurate three-dimensional model reconstruction of small-scale objects with application to wounds may be achieved through the following method as described below.

First, relative camera poses between different two-dimensional images need to be estimated. Second, based on the estimated poses, the image points on the two-dimensional images can be back-projected onto the three-dimensional space. The intersections of the back-projected rays determine the three-dimensional points and the reconstructed three-dimensional model. In this method, improving the estimation of relative camera poses may be the most important factor to achieve good accuracy in SfM.

Relative camera poses estimation involves several steps. In particular, a robust model estimation algorithm needs to be applied to estimate the relative geometric transformation between the two-dimensional images and remove outlier correspondences. Embodiments include applying sophisticated sampling and model checking and verification to significantly improve the accuracy in model estimation and reduce the computational complexity.

In addition, current smartphone gyroscope and accelerometer sensors can produce crude values for camera intrinsic parameters. Many digital cameras also embed focal length and other information in the exchangeable image file format (EXIF) tags of image files. Such information can be used at the server implementing the second trained deep neural network to capture rough camera movements and therefore increase the speed of convergence by setting value limits to the amount each pixel could have been moved from one digital image to another. This limit significantly reduces the point matching time at the server side.

At step C of FIG. 2, the processor module 202 may determine at least one critical dimension of the wound based on the segmented three-dimensional model. A critical dimension includes at least one of a wound length, wound width and wound depth, which can be calculated from the localized three-dimensional wound region. The segmented three-dimensional model may be attained from the combination of the segmentation of the wound from other surrounding tissue of the wound in the digital images (step B of FIG. 2) and construction of the three-dimensional model of the wound (step C of FIG. 2).

More specifically, a plurality of feature vectors from the digital images may be extracted. For example, each three-dimensional point is associated with one or more local feature descriptors or vectors (e.g. using scale-invariant feature transform, SIFT). Local features in the two-dimensional images can be matched against those of the three-dimensional points. This matching registers the two-dimensional images onto the three-dimensional model. After the two-dimensional images are registered, wound region boundary can be identified in the three-dimensional model based on the two-dimensional segmentation results.

Active corresponding search may be used in this regard for two-dimensional to three-dimensional feature matching, which may reduce computational complexity. In addition, current smartphone gyroscope and accelerometer sensors can produce crude values for camera intrinsic parameters. Many typical digital cameras also embed focal length and other information in the EXIF tags of image files. Such information may be used at the server to capture rough camera movements and therefore increase the speed of convergence by setting value limits to the amount each pixel could have been moved from one image to another. The value limits may significantly reduce the point matching time at the server side. Thereafter, critical dimensions of the wound, such as the wound area and depth, can be attained using the localized three-dimensional wound region and camera intrinsic information.

At step D of FIG. 2, after the feature vectors are extracted and critical dimensions of the wound are determined, a first deep neural network module 204 that is configured to implement a first trained deep neural network identifies a type of wound tissue based on the plurality of extracted feature vectors.

Wound tissue analysis is important to diagnose the wound type and decision on treatment. Embodiments advantageously enable identification of the following seven types of wound tissues: necrotic, slough, healthy granulation, unhealthy granulation, hyper granulation, infected and epithelization.

Necrotic is the dry dead tissue and is black in color and occurs when skin cells inside of the wound die off. The sloughy tissue is a type of wet necrotic tissue that is detaching itself from the wound site, and is often seen white, yellow or grey in color. Healthy granulating is the new grown tissue that is generated when the wound surface area is starting to heal by tiny blood vessels that appear at the surface, with light red or pink in color, and will be moist. Unhealthy granulating tissue is when the process of granulation is irritated by problems such as infection or lack of good blood supply, and appears dark red, bluish, or very pale, and may indicate ischemia or infection in the wound. Hyper-granulating tissue is the tissue that grows above the wound margin and skin level when the proliferative phase of healing is prolonged usually as a result of bacterial imbalance or irritant forces. Infected tissue is greenish color tissue with foul smell caused by bacterial infection that may spread to different parts of the wound and it surrounding tissues. Finally, epithelizing tissue is a group of tightly-packed cells that provides protective layers over the granulating tissue.

Figure 5:
FIG. 5 shows a diagram of an identification of a wound by a first deep neural network, according to an example embodiment.

The system as claimed may detect all seven types of wound tissues. The first trained deep neural network may determine the tissue type of each pixel. In other words, the first trained deep neural network may be used as a pixel classifier such that it is a max-pooling convolutional neural network. The first trained deep neural network takes a small, square patch of pixels as input, where the patch can be a uniform patch or a segment of the digital image. The digital image can be a visible light image, or a combination of visible and thermal images that are combined to form a single digital image. The patch provides context information for the central pixel and the first trained deep neural network determines the class label of the central tissue pixel (or majority of the pixels in the patch). The tissue pixels in the wound are classified with a sliding window approach and the first trained deep neural network automatically learns a set of visual features from the training data. Thus, with a big dataset of training data, first trained deep neural network can mine rich and discriminative visual features beyond color and texture for this classification task as shown FIG. 5.

The following method addresses typical problems in training deep neural networks to identify the type of wound tissue. An example of a problem includes training such several deep neural networks on limited number of medical data, without facing an overfitting problem. Another example is to compress the resulting trained networks to run them on a smartphone that has limited computational power, memory, and energy.

The first step of the method is to train the first deep neural network based on how the human brain perceive images. Humans perceive color of an object to be similar under different lighting conditions, which is a result of a process in the early visual cortex that also shown in "color illusion experiments". In order to replicate such a perception consistency, the first deep neural network is trained using approximately a thousand images that have the same scene under different illumination (as shown in section X of FIG. 6). These images are unrelated to the wound, but help the first deep neural network to learn the color consistency under different illumination conditions.

Figure 6:
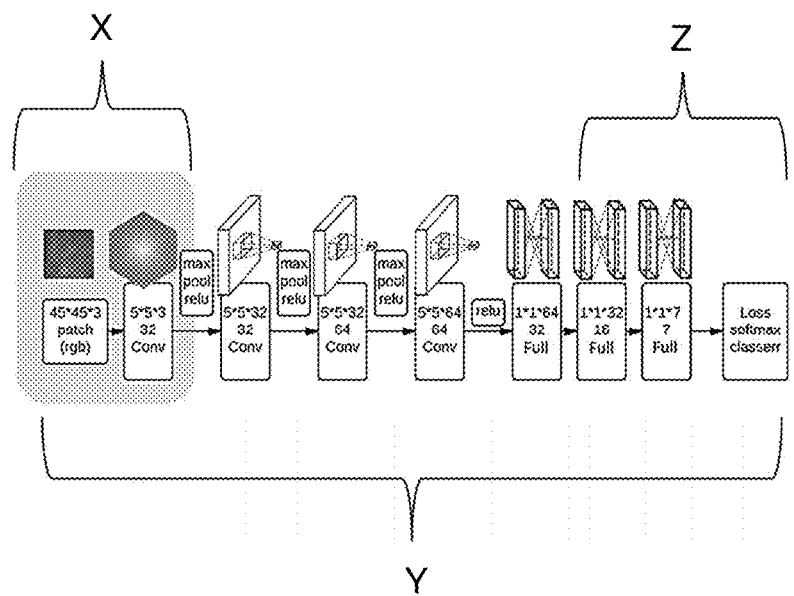
FIG. 6 shows a flow chart illustrating a method of training a first deep neural network, according to an example embodiment.

Subsequently, the first deep neural network is trained on general object detection using over 1.2 million images of a thousand different objects (unrelated to the wound) from a public image database (for example ImageNet) as shown in Section Y of FIG. 6. This trains the first deep neural network to pick up different aspects of an "object" including lines and curves, color, texture, etc. As the first deep neural network is now trained to be robust under different illuminations and general characteristics of an "object", the first deep neural network is trained specifically on wound images to fine-tune the higher-level decisions in the network on distinguishing different wound or tissue types (see Section Z of FIG. 6).

A joint segmentation-tissue analysis approach may also be used to train the first deep neural network. More specifically, in background-skin-wound segmentation, over-segmentation of the wound is carried out to obtain smaller partitions of the skin/wound. Each partition may be normalized in size and then be passed directly into the first deep neural network for classification into skin/wound tissue classes. The first deep neural network assigns the same label for all the tissue pixels belonging to the same partition.

The first deep neural network can be trained such that the background-skin-wound segmentation and wound tissue segmentation may be included in a single architecture. The first deep neural network can receive the thermal image corresponding to the visible light as an additional channel to the visible light image so that it may achieve better segmentation/tissue labelling results. It is also possible to receive an infrared signature directly from the visible light camera on the smartphone without having the thermal attachment. This can be accomplished by removing the infrared filter on the phone camera and the unfiltered image would be then the input of the first deep neural network to output the tissue labels. In order to run the network efficiently on a portable device (such as a smartphone), the first deep neural network is compressed through quantization and hashing of variables which can compress the network size up to ten times from the normal size while increasing its speed up to three times from the normal speed.

In an alternative embodiment, two-dimensional image synthesis may be used to argument the training dataset: Using such a method, the same wound can be imaged in different lighting conditions, with different devices, and in different camera settings, and thus creating different images with possibly different characteristics. By estimating how a wound would look like under these different situations, the training database size can be increased exponentially. Image processing methods and computational photography fields may be used for synthesizing images in the training dataset. In other words, an image taken by a certain device and in a certain camera setting may be transferred to any other device and in any camera settings.

In yet another embodiment, realistic motion-blur synthesis may be used as a set of images to the image database. This is because many of the images taken by portable devices are prone to motion-blur, and therefore the first trained deep neural network should handle this type of imaging artefact. Typical de-blurring techniques include using real motion kernels, recorded using accelerometers. These motion kernels can be used to re-generate blurred images from original database images, as if they were actually captured while the portable device was moving. This set of synthesized images can not only help increase the image database size, it can also develop a classification model robust to these artefacts. The same approach can be applied to other types of imaging artefacts such as noise and poor lighting.

At step E in FIG. 2, the processor module 202 may be configured to extract thermal signature data from the thermal image and identify a secondary complication based on the extracted thermal signature data. The secondary complication may comprise at least one of: blood-circulation, wound infection, skin-related condition, undermining of wound and pressure point.

Visible and Thermal signatures (VTS) of skin and wound can change due to various medical conditions including the healing process, fighting with the infections, chemical deposits in the skin (due to disruptions in the normal of different organs such as kidney or liver). These changes in VTS can be correlated with different medical conditions such as different states of healing, whether the wound is improving or degrading or infected, whether these are signs of early complications, or even signs of states that lead to specific complications (such as bed sores, gangrene, diabetes, etc.).

In an embodiment, a large volume of data with visible images and corresponding temperature images are collected to estimate temperature of the wounds, skin surrounding wound regions (peri-wound), and even normal-looking limbs. Subsequently, correlation is carried out with the collected VTS data with different medical states (either current or temporally in future). Based on a large number of sparsely temperature-tagged images, estimation of the relative heat-map of the skin/wound may be achieved based on the observed pixel values. Although the changes in visible or thermal signature may not be detectable by the naked eye, a systematic search for VTS signatures in an ordinary digital image of the wound may be conducted using advanced signal mining approaches. Subsequently, based on the literature and also the individual history of the wound/skin/patient condition in the database, a predictive model may be used to predict current as well as future medical states using the estimated VTS.

Figure 7:
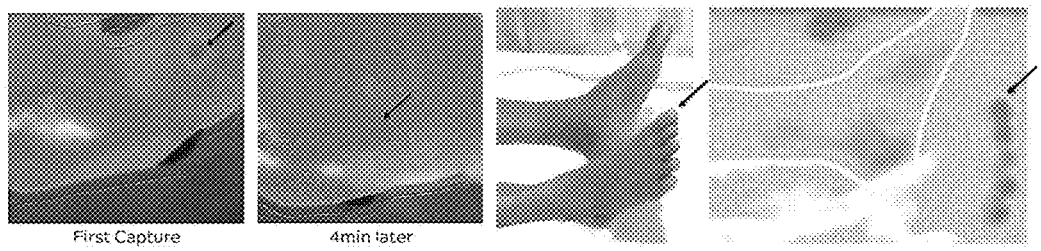
FIG. 7 shows images of a secondary complication during identification based on the extracted thermal signature data, according to an example embodiment.

In an embodiment, the processor module 202 can automatically identify different wound related complications through modelling of instant VTS or temporal changes in VTS. This may be applicable to both complication management (e.g. monitoring of an infected wound) and preventive care (early blood circulation disruption, changes in the skin prior to diabetes or wound formation). For example, as shown in FIG. 7, the processor module 202 can detect blood circulation problems in a limb (below, left), or pressure points on the skin (below, right) that can eventually develop a wound.

Figure 8:
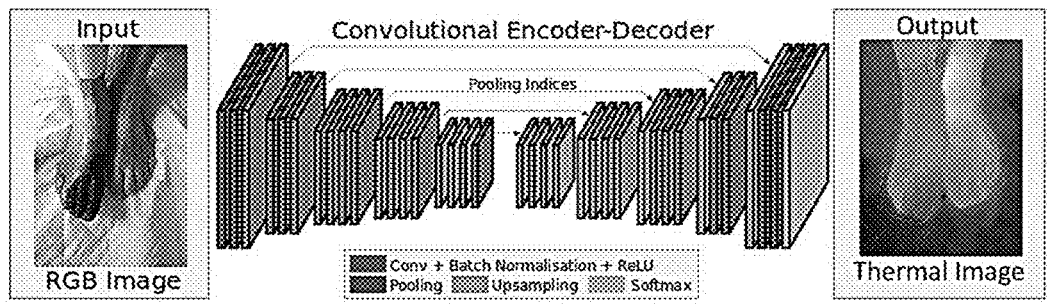
FIG. 8 shows a schematic diagram of an image processing procedure, according to an example embodiment.

In an embodiment, a large volume of data with temperature tags is used to estimate temperature of the wound, relative to its surrounding skin regions, and correlation is carried out between the relative temperature estimation and different states of the wound healing. Based on a large number of visible-infrared image pairs as well as sparsely temperature-tagged images, estimation is carried out on the relative heat-map of the skin in accordance with the observed color. The visible-infrared image pairs may be captured using portable devices and attached thermal camera. A Deep Auto Encoder (DAE) architecture is used with images from a digital camera, and the corresponding thermal image captured by the phone attachment is sent (see FIG. 8). Although the color changes may not be visible by the naked eye, heat signatures can be searched in an ordinary digital image of the wound using advanced signal mining approaches. Different models of RGB may be used to heat-map transfer based on the content of the image. For example, the image sections that contain human body has a different model than sections of images that contain background.

Figure 9:
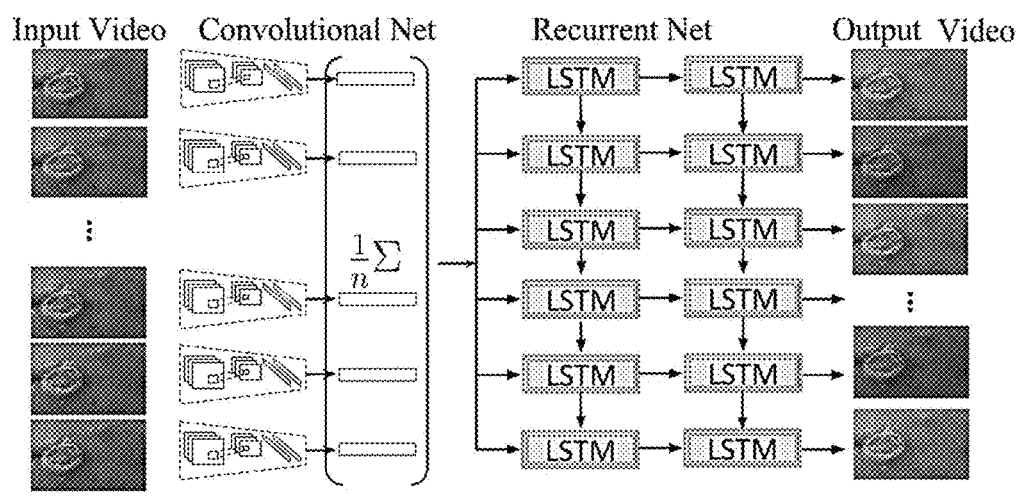
FIG. 9 shows a video magnification procedure for detecting blood circulation of a wound, according to an example embodiment.

Blood circulation may be interrupted in and around the wound due to severed/blocked veins. The blood circulation patterns also change around the wound as the body is fighting infections. Therefore, detection of blood circulation patterns may be used in estimating the wound status. As shown in FIG. 9, a video magnification method may reveal the pulse from a video of skin, by amplification of temporal variations in videos that are difficult or impossible to see with the naked eye. In this method, spatial decomposition, followed by temporal filtering is applied to the sequence of frames. Given the normal frequency of the human heartbeat, filtration can be accomplished using the video taken from a body part and magnify the color changes on the skin due to the blood circulation (pulse), as well as the path the blood is taking.

In an embodiment, a Recursive Convolutional Neural Network (RCNN) may be used to replicate the same results, but with significantly lower complexity, near real-time, and robust to uncontrolled environments, and suitable for running on portable devices such as smartphones. The input and output from the video magnification method is used with fitted parameters for human pulse rate and skin color changes. The network is trained to produce the same resulted magnified pulse output given the video of the skin. When the skin color shifts due to blood circulation are detected, the flow of the blood throughout the skin can be estimated. In another embodiment, such a structure can be combined with wound segmentation to focus color change amplification to the skin and wound areas, to subsequently obtain the optical flow related to the blood circulation.

After the second neural network module 206 determines the dimension of the wound, the processor module 202 receives wound data corresponding to one or more of: (i) the identified type of wound tissue, (ii) the dimension of the wound, and (iii) the identified secondary complication. The processor module 202 then generates a coded vector based on the wound data using a deep hashing function. The coded vector may represent a consolidated assessment of the wound and/or a profile of the target subject.

More specifically, the deep hashing function may provide several codes for any received wound data and/or a profile of the target subject (e.g. a patient profile). Each of the received wound data, such as wound type, wound dimension and secondary complication as well as the target subject profile, is a vector of values obtained directly from the network within the respective modules and not in any specific human understandable format. These value vectors are distinct from the human understandable reports that are created based on measurement outputs of these modules. These vectors are one or more layers of the deep neural structures that are used in these modules, and not a single value. The processor module 202 receives all of such value vectors and generates a coded vector that defines the current state of the current case. The coded vector is then stored at the database 210, which in communication with the processor module 202. The generated coded vector may be used to estimate the condition of the care, and predict the healing process, and also to match to any other case to select the top most relevant cases in the database 210, to a query case.

In an embodiment, the processor module 202 may generate a coded vector that includes several sub-values. The first sub-value may be a single value that shows the current collective state of the case in terms of healing. The subsequent sub-values are predicted values for collective healing state (e.g. for one week, two weeks, and one month in the future). As these sub-values are determined by the coded vector and the coded vector contains both the current assessments of the current wound and profile of the target subject, the resulting healing state estimation is affected by all these factors. The processor module 202 may be trained by using the coded vector as input together with the actual collective healing state by clinical professionals. Each medical condition has a different model (e.g. wound models are different skin condition models). The sub-values can be used to track and predict the healing state of each case.

At step F in FIG. 2, the processor module 202 retrieves treatment data corresponding to the coded vector from the database 210. In other words, the processor module 202 matches the query coded vector and retrieves the best matching cases found in the database 210. The matched data may be presented to the target subject and/or a user through a user device (not shown in FIG. 2). The matching is performed in three steps. The first step is the condition matching, e.g. wounds, blood circulation problems, skin conditions, etc. The second step is cluster matching, which finds the best matching cluster of data in the database 210 to the query coded vector. The third and final step is to find the top matches inside the cluster of samples and return them to be presented to the user. The three step matching process may increase the accuracy of matching as well as substantial reduction in search time. In addition, the current system uses different neural network modules located on both front-end on portable devices (e.g. smartphone) and back-end on server, the data stored in the database 210 is the data that links these the different modules and is not human understandable, thus making the stored data secure even in the event that they are leaked to external sources.

Use of the term "module" herein may be understood to mean a single computing device or a plurality of interconnected computing devices which operate together to perform a particular function. That is, the module may be contained within a single hardware unit or be distributed among several different hardware units. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

An exemplary computing device which may be operated as a module is described below with reference to FIG. 10.

Figure 10:
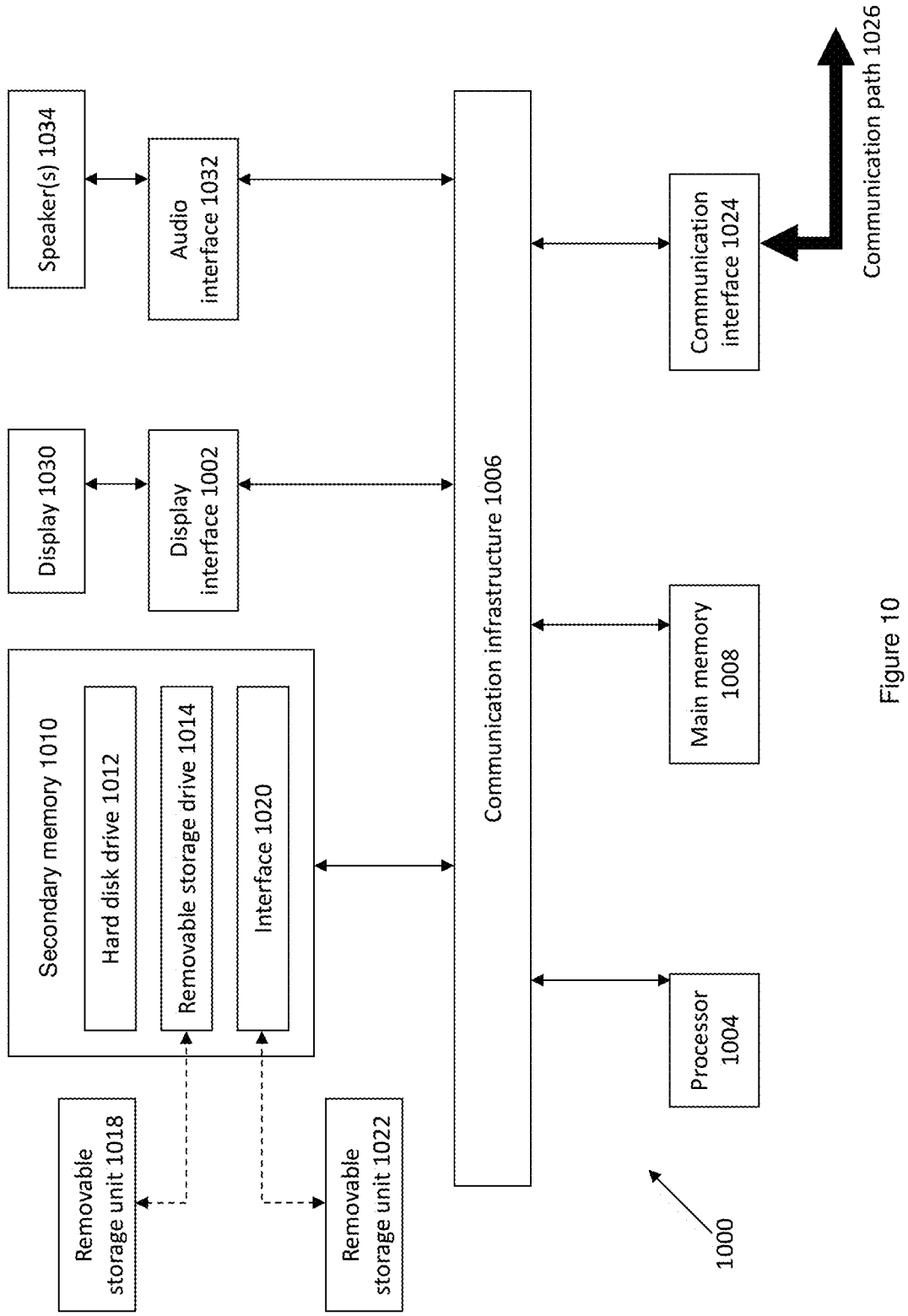
FIG. 10 shows a schematic diagram of a computer device/system suitable for realizing a module, according to an example embodiment.

FIG. 10 shows a schematic diagram of a computer device or computer system 1000 suitable for realizing the processor module 202, the first neural network module 204, the second neural network module 206 and/or the image capturing module 208. The following description of the computing device 1000 is provided by way of example only and is not intended to be limiting.

As shown in FIG. 10, the example computing device 1000 includes a processor 1004 for executing software routines. Although a single processor is shown for the sake of clarity, the computing device 1000 may also include a multi-processor system. The processor 1004 is connected to a communication infrastructure 1006 for communication with other components of the computing device 1000. The communication infrastructure 1006 may include, for example, a communications bus, cross-bar, or network.

The computing device 1000 further includes a main memory 1008, such as a random access memory (RAM), and a secondary memory 1010. The secondary memory 1010 may include, for example, a hard disk drive 1012, which may be a hard disk drive, a solid state drive or a hybrid drive and/or a removable storage drive 1014, which may include a magnetic tape drive, an optical disk drive, a solid state storage drive (such as a USB flash drive, a flash memory device, a solid state drive or a memory card), or the like. The removable storage drive 1014 reads from and/or writes to a removable storage unit 1018 in a well-known manner. The removable storage unit 1018 may include magnetic tape, optical disk, non-volatile memory storage medium, or the like, which is read by and written to by removable storage drive 1014. As will be appreciated by persons skilled in the relevant art(s), the removable storage unit 1018 includes a computer readable storage medium having stored therein computer executable program code instructions and/or data.

In an alternative implementation, the secondary memory 1010 may additionally or alternatively include other similar means for allowing computer programs or other instructions to be loaded into the computing device 1000. Such means can include, for example, a removable storage unit 1022 and an interface 1020. Examples of a removable storage unit 1022 and interface 1020 include a program cartridge and cartridge interface (such as that found in video game console devices), a removable memory chip (such as an EPROM or PROM) and associated socket, a removable solid state storage drive (such as a USB flash drive, a flash memory device, a solid state drive or a memory card), and other removable storage units 1022 and interfaces 1020 which allow software and data to be transferred from the removable storage unit 1022 to the computer system 1000.

The computing device 1000 also includes at least one communication interface 1024. The communication interface 1024 allows software and data to be transferred between computing device 1000 and external devices via a communication path 1026. In various embodiments, the communication interface 1024 permits data to be transferred between the computing device 1000 and a data communication network, such as a public data or private data communication network. The communication interface 1024 may be used to exchange data between different computing devices 1000 which such computing devices 1000 form part an interconnected computer network. Examples of a communication interface 1024 can include a modem, a network interface (such as an Ethernet card), a communication port (such as a serial, parallel, printer, GPIB, IEEE 1394, RJ45, USB), an antenna with associated circuitry and the like. The communication interface 1024 may be wired or may be wireless. Software and data transferred via the communication interface 1024 are in the form of signals which can be electronic, electromagnetic, optical or other signals capable of being received by communication interface 1024. These signals are provided to the communication interface via the communication path 1026.

As shown in FIG. 10, the computing device 1000 further includes a display interface 1002 which performs operations for rendering images to an associated display 1030 and an audio interface 1032 for performing operations for playing audio content via associated speaker(s) 1034.

As used herein, the term "computer program product" may refer, in part, to removable storage unit 1018, removable storage unit 1022, a hard disk installed in hard disk drive 1012, or a carrier wave carrying software over communication path 1026 (wireless link or cable) to communication interface 1024. Computer readable storage media refers to any non-transitory tangible storage medium that provides recorded instructions and/or data to the computing device 1000 for execution and/or processing. Examples of such storage media include magnetic tape, CD-ROM, DVD, Blu-Ray™ Disc, a hard disk drive, a ROM or integrated circuit, a solid state drive (such as a USB flash drive, a flash memory device, a solid state drive or a memory card), a hybrid drive, a magneto-optical disk, or a computer readable card such as a PCMCIA card and the like, whether or not such devices are internal or external of the computing device 1000. Examples of transitory or non-tangible computer readable transmission media that may also participate in the provision of software, application programs, instructions and/or data to the computing device 1000 include radio or infra-red transmission channels as well as a network connection to another computer or networked device, and the Internet or Intranets including e-mail transmissions and information recorded on Websites and the like.

The computer programs (also called computer program code) are stored in main memory 1008 and/or secondary memory 1010. Computer programs can also be received via the communication interface 1024. Such computer programs, when executed, enable the computing device 1000 to perform one or more features of embodiments discussed herein. In various embodiments, the computer programs, when executed, enable the processor 1004 to perform features of the above-described embodiments. Accordingly, such computer programs represent controllers of the computer system 1000.

Software may be stored in a computer program product and loaded into the computing device 1000 using the removable storage drive 1014, the hard disk drive 1012, or the interface 1020. Alternatively, the computer program product may be downloaded to the computer system 1000 over the communications path 1026. The software, when executed by the processor 1004, causes the computing device 1000 to perform functions of embodiments described herein.

It is to be understood that the embodiment of FIG. 10 is presented merely by way of example. Therefore, in some embodiments one or more features of the computing device 1000 may be omitted. Also, in some embodiments, one or more features of the computing device 1000 may be combined together. Additionally, in some embodiments, one or more features of the computing device 1000 may be split into one or more component parts.

Figure 11:
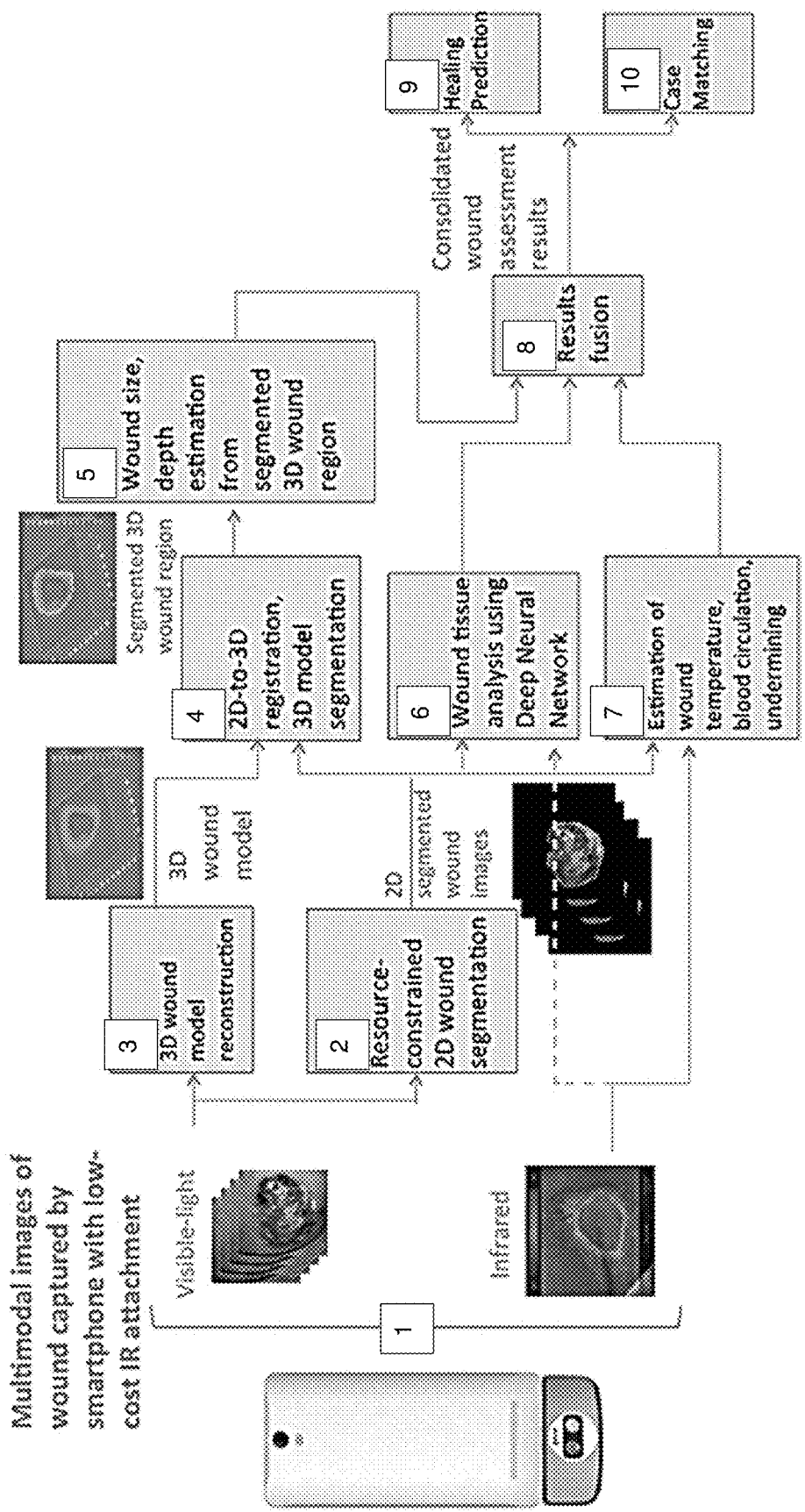
FIG. 11 shows a schematic diagram illustrating the flow of information between various entities during a method for facilitating analysis of a wound of a target subject, according to an example embodiment.

FIG. 11 shows a schematic diagram illustrating the flow of information between various entities during a method for facilitating analysis of a wound of a target subject, according to an example embodiment. At step 1, a portable device, such as a smartphone, captures digital images of a wound of a target subject. The smartphone may include an infrared camera attachment such that the digital images captured include but are not limited to an infrared image and a visible-light image. At step 2, the digital images are processed and the wound is segmented from the surrounding tissue. At step 3, a three-dimensional model of the wound is constructed. At step 4, the three-dimensional model is processed to segment the wound from the surrounding tissue. At step 5, after segmentation of the wound, critical dimensions of the wound, such as the wound size and depth are determined.

At step 6, which may occur is parallel to step 4, a type of wound tissue is identified by a deep neural network. At step 7, a secondary complication of the wound, such as wound temperature, blood circulation, undermining and pressure point, is identified. At step 8, the results of the wound dimensions, wound tissue type and secondary complication are consolidated and assessed. At step 9, a predicted time of healing is provided based on the collected results in step 8. At the same time in step 10, a similar case that matches the current wound data is retrieved from the database based on the collected results in step 8.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method for facilitating analysis of a wound of a target subject, comprising:
    obtaining one or more digital images of at least a portion of the wound;
    processing the one or more digital images, using a first trained deep neural network, the first trained deep neural network comprising a convolutional neural network that is trained on illumination variations, the first trained deep neural network being configured to identify one or more of seven types of wound tissues based on the plurality of extracted feature vectors;
    extracting a plurality of feature vectors from the one or more processed digital images; and
    identifying, using the first trained deep neural network, at least one of the one or more of seven types of wound tissues based on the plurality of extracted feature vectors,
    wherein the seven types of wound tissues consists of: necrotic, slough, healthy granulation, unhealthy granulation, hyper granulation, infected and epithelization.

2. The method according to claim 1, the method further comprising:
    processing the one or more digital images of the wound for segmentation of the wound from other surrounding tissue of the wound prior to extracting the plurality of feature vectors from the one or more digital images.

3. The method according to claim 2, wherein the step of processing the one or more digital images of the wound for segmentation of the wound comprises:
    down-sampling the one or more digital images of the wound;
    coarse segmentation of the down-sampled one or more digital images; and
    refinement of the coarse segmented one or more digital images.

4. The method according to claim 1, wherein two digital images of the wound are obtained separately from two digital image capturing devices spaced apart from each other, wherein the method further comprises:
    constructing a three-dimensional model of the wound based on the two digital images of the wound; and
    processing the three-dimensional model of the wound for segmentation of the wound from other surrounding tissue of the wound to generate a segmented three-dimensional model prior to extracting the plurality of feature vectors from the one or more digital images.

5. The method according to claim 4, the method further comprising:
    determining at least one critical dimension of the wound based on the segmented three-dimensional model.

6. The method according to claim 5, wherein one of the two digital images comprises a thermal image of the wound, wherein the method further comprises:
    extracting thermal signature data from the thermal image; and
    identifying a secondary complication based on the extracted thermal signature data.

7. The method according to claim 6, wherein the secondary complication comprises at least one of: blood-circulation, wound infection, skin-related condition, undermining of wound and pressure point.

8. The method according to claim 6, the method further comprising:
    receiving wound data corresponding to one or more of: (i) the identified type of wound tissue, (ii) the dimension of the wound, and (iii) the identified secondary complication;
    generating a coded vector based on the wound data using a deep hashing function, the coded vector representing a consolidated assessment of the wound;
    retrieving, from a database, treatment data corresponding to the coded vector.

9. The method according to claim 4, wherein a second trained deep neural network is used to facilitate construction of the three-dimensional model of the wound.

10. A system for facilitating analysis of a wound of a target subject, comprising:
    one or more image capturing modules configured to obtain one or more digital images of at least a portion of the wound;

a first neural network module configured to implement a first trained deep neural network for processing the one or more digital images, the first trained deep neural network comprising a convolutional neural network that is trained on illumination variations; and a processor module configured to extract a plurality of feature vectors from the processed one or more digital images, wherein the first trained deep neural network is further configured to identify one or more of seven types of wound tissues based on the plurality of extracted feature vectors;

wherein the seven types of wound tissues consists of: necrotic, slough, healthy granulation, unhealthy granulation, hyper granulation, infected and epithelization.

11. The system according to claim 10, wherein the processor module is further configured to process the one or more digital images of the wound for segmentation of the wound from other surrounding tissue of the wound prior to extracting the plurality of feature vectors from the one or more digital images.

12. The system according to claim 11, wherein the processor module is further configured to:

perform down-sampling the one or more digital images of the wound;

perform coarse segmentation of the down-sampled one or more digital images; and perform refinement of the coarse segmented one or more digital images, for segmentation of the wound from other surrounding tissue of the wound.

13. The system according to claim 10, further comprising two digital image capturing devices spaced apart from each other and configured to separate obtain two digital images of the wound, wherein the processor module is further configured to:

construct a three-dimensional model of the wound based on the two digital images of the wound; and process the three-dimensional model of the wound for segmentation of the wound from other surrounding tissue of the wound to generate a segmented three-dimensional image prior to extracting the plurality of feature vectors from the one or more digital images.

14. The system according to claim 13, wherein the processor module is further configured to:

determine at least one critical dimension of the wound based on the segmented three-dimensional model.

15. The system according to claim 14, wherein one of the two digital images comprises a thermal image of the wound, wherein the processor module is further configured to:

extract thermal signature data from the thermal image; and identify a secondary complication based on the extracted thermal signature data.

16. The system according to claim 15, wherein the secondary complication comprises at least one of: blood-circulation, wound infection, skin-related condition, undermining of wound and pressure point.

17. The system according to claim 15, wherein the processor module is further configured to:

receive wound data corresponding to one or more of: (i) the identified type of wound tissue, (ii) the dimension of the wound, and (iii) the identified secondary complication;

generate a coded vector based on the wound data using a deep hashing function, the coded vector representing a consolidated assessment of the wound;

retrieve, from a database, treatment data corresponding to the coded vector.

18. The system according to claim 13, further comprising a second neural network module configured to implement a second trained deep neural network to facilitate construction of the three-dimensional model of the wound.

* * * * *